United States Patent [19]

Robertson et al.

[11] Patent Number: 5,268,292

[45] Date of Patent: Dec. 7, 1993

[54] REPRODUCIBLE GENERATION OF HIGH YIELDS OF HEPATITIS A VIRUS BY CELL CULTURE

[76] Inventors: Betty H. Robertson, 2992 Stratford Arms Dr., Chamblee, Ga. 30341; Rhawna Khanna, 4133 Church St. Apt. G4, Clarkston, Ga. 30021; Vicki Brown, 2499 Old Orchard St., Dunwoody, Ga. 30338; Harold S. Margolis, 5254 Silver Creek Dr., Lilburn, Ga. 30247

[21] Appl. No.: 758,470

[22] Filed: Sep. 6, 1991

Related U.S. Application Data

[63] Continuation of Ser. No. 211,973, Jun. 27, 1988, abandoned.

[51] Int. Cl.$^5$ .................. C12P 21/02; C12P 19/34; C12N 7/00; C12N 5/00
[52] U.S. Cl. .................. 435/240.2; 435/69.3; 435/235.1; 435/91.33; 536/23.72; 935/32; 935/34; 935/57; 935/65; 935/70
[58] Field of Search .................. 435/69.3, 91, 172.3, 435/235.1, 240.2; 536/27; 530/350; 935/12, 32, 34, 57, 65, 70

[56] References Cited

U.S. PATENT DOCUMENTS

| | | | |
|---|---|---|---|
| 4,301,249 | 11/1981 | Markus et al. | 435/235 |
| 4,506,016 | 3/1985 | Flehmig | 435/237 |
| 4,532,215 | 7/1985 | Daemer et al. | 435/237 |
| 4,596,674 | 6/1986 | Emini et al. | 530/326 |
| 4,616,793 | 9/1986 | Hughes et al. | 530/350 |
| 4,620,978 | 11/1986 | Daemer et al. | 424/89 |
| 4,636,469 | 1/1987 | Daemer et al. | 435/237 |
| 4,721,675 | 1/1988 | Chan et al. | 435/239 |
| 4,861,706 | 8/1989 | Hurni et al. | 435/5 |
| 4,894,228 | 1/1990 | Purcell et al. | 424/89 |
| 5,021,348 | 6/1991 | Giesa et al. | 435/237 |

OTHER PUBLICATIONS

Anderson et al. J. Cell. Biochem. vol. 10D p. 287 (1986).

Primary Examiner—Joan Ellis
Attorney, Agent, or Firm—Cushman, Darby & Cushman

[57] ABSTRACT

The invention is a process for cell propagation of hepatitis A virus. The process involves purifying a culture of hepatitis A virus particles. These hepatitis A virus particles are used for infecting cells being cultivated in a media. The hepatitis A particles suitable for use in this invention must have a cytopathic effect in the infected host cells that are selected for culturing the hepatitis A virus. After developing the cytopathic effect in the infected cells, the hepatitis A viruses produce degeneration and lysis in the infected cells and are released into the media. Isolation of the released hepatitis A virus then occurs. The preferred cells for use in this invention are FRhK4 (foetal rhesus monkey kidney) cells. The preferred virus particles for use in this invention are hepatitis A, strain HAS-15 particles have an antigen coded by a nucleotide sequence according to FIG. 1.

4 Claims, 7 Drawing Sheets

FIG. I

```
          10        20        30        40        50        60        70
A.) GTTGGAGATGATTCAGGAGGTTCTCAACAACAGTTTCTACAGAGCAGAATGTTCCTGATCCCCAAGTTGGCATA
B.) ..........................................................................G 80        90       100
    --------AAAGGGA
    ---------------

AAGCCAATAGGGGAAAGATGATGTATCAGGAGTGCAGGCACCTGTGGGAGCTATTACAACAATTGAGGATCCAG
........................................................................

TTTTAGCAAAGAAAGTACCTGAGAC
.........................

ATTTCCTGAATTGAAGCCTGGAGAATCCAGACATACATCAGATCACATGTCTATTTATAAATTCATGGGAAGGTC
............................................................................

TCATTTCTTGTGTACTTTTACTTTT
.........................
```

FIG. 1 (cont.)

```
AATTCAAACAATTTGAGTACACATTCCAATAACTCTCTGTCTTCGACTTCTAATCCTCCTCATGGTTACCATCA
ACATTAAGGTGGTTCTTTAATTTGT
TTCAGTTGTATAGAGGACCATTGGATTTGACAATTATAATCACAGGAGCCACTGATGTGGATGGTATGGCCTGGT
TTACTCCAGTGGGCCTTGCTGTCGA
```

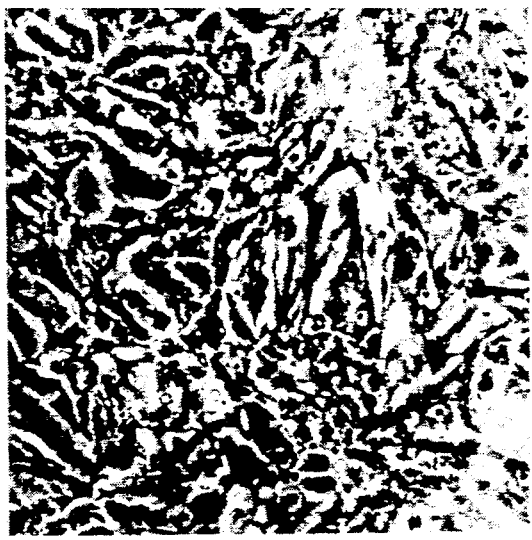
FIG. 6C (Persistent)
FIG. 6B (Acute)
FIG. 6A (Uninfected)

REPRODUCIBLE GENERATION OF HIGH YIELDS OF HEPATITIS A VIRUS BY CELL CULTURE

This is a continuation of application Ser. No. 07/211,973, filed on Jun. 27, 1988, which was abandoned upon the filing hereof.

BACKGROUND OF THE INVENTION

1. Field of the Invention

This invention relates to a method for reproducibly generating hepatitis A virus (HAV) in high (milligram) yields. Specifically, this invention relates to a process for cytopathically generating a hepatitis A virus in a cell line.

2. Description of the Background Art

An propagated in persistently-infected cells has traditionally been used to generate antigen for immunodiagnostic purposes such as HAVAB kits produced by Abbott Laboratories in North Chicago, Ill. A single milligram of HAV using their system has been estimated as costing $25,000 (K. Watson, 1984), and involving a single person full-time for a year for virus purification.

Since the first demonstration of cell culture growth of hepatitis A virus (HAV) by Provost and Hilleman (1979), there have been numerous reports describing conditions for growth of HAV in various cell lines and under various conditions (Flehmig, 1980; 1981; Flehmig et al., 1981; Daemer et al., 1981; Gauss-muller et al., 1984; Bradley et al., 1984; Vallbracht et al., 1984; Simmons et al., 1985; Wheeler et al., 1986a). After initial adaptation of the virus to the appropriate cell line, the growth of hepatitis A virus in cell culture has been reported as being non-cytopathic and usually results in a persistent infection in which both cells and virus coexist in a symbiotic relationship. Quantitation of virus present within persistently infected cells determined by cell culture infectivity or physical particle counts has varied from $10^5$ virus particles/ml up to $10^{10}$ virus particles/ml (Binn et al., 1984; Simmons et al., 1985; Wheeler et al., 1986a, b). Recently there have been reports of HAV in cell culture producing degeneration of host cells (Venuitti et al., 1985; Shen et al., 1986; Anderson et al., 1986; 1987; Cromeans et al., 1987). The conditions necessary to produce the cytopathic effect in each system appear to be cell and growth condition specific and the quantity of purified virus obtained has not been reported.

A human fecal sample obtained during the acute phase of hepatitis A infection and propagated in FRhK4 cells was designated HAS-15 (Bradley et al., 1984). The quantity of virus produced, as evaluated by radioimmunoassay, appeared to increase with passage, while the time required for viral growth decreased. Subsequently, the ninth passage of this strain was passaged more than 20 times at 7-day intervals to select for a rapidly growing virus population (Wheeler et al., 1986a). Using large scale virus propagation methods, the purified virus derived from these persistently-infected cells was used to characterize the HAV capsid polypeptides (Wheeler et al., 1986b). The initial yield from 350 liters of cell supernatant and the cell lysates from $1 \times 10^6$ cm$^2$ of cells was approximately 5 mg of purified virus (Wheeler et al., 1986b), although subsequent recoveries were substantially lower.

The adaptation of HAV for growth in cell culture from fecal samples has been shown to require an initial protracted lag or eclipse phase (Frosner et al., 1979; Daemer et al., 1981; Gauss-Muller et al., 1981; Binn et al., 1984; and Bradley et al., 1984) varying from 4 weeks to 12 weeks. After adaptation, which can be dependent upon the type of cells and/or the titer of the original inocula, passage of virus-positive cell lysates or supernatants, results in a decrease in the time needed for detectable viral growth and an apparent increase in the amount of virus produced. However, in none of these reports has there been any evidence of cytotoxicity associated with HAV replication.

In contrast to the early extended time periods needed for adaptation of virus from clinical specimens, cell-culture adapted virus becomes detectable by immunoassay or immunofluorescence within 1-17 days (Vallbracht et al., 1985; Simmonds et al., 1985; Wheeler et al., 1986a; and Cromeans et al., 1987) and this relatively rapid growth has been utilized to grow HAV by passage of persistently-infected cells (Vallbracht et al., 1984; Simmonds et al., 1985; and Wheeler et al., 1986b). However, although persistent infection has been purported to be the most practical method to grow HAV, the data indicates that over a period of time there was a significant decrease in the amount of virus produced by persistently infected cells. The cause of this decrease was not clear. One explanation was that over a long period of time, cells more sensitive to HAV growth were destroyed by infection, and a population of cells resistant to HAV infection was selected. This would explain the decreased virus production and the observation that the majority of the virus was cell-associated.

A previous report from the inventors' laboratory indicated that persistent infection of FRhK4 cells can produce large quantities of virus (Wheeler et al., 1986b), however, the time course data and ongoing experience suggests that this method does not sustain high-yield production of virus and that the major portion of the virus was probably obtained from the early phase of the persistent infection as well as from the acute infection used to initiate the persistently infected cells.

There are now four examples of cytopathic infection with HAV isolates which have been reported (Venutti et al., 1985; Shen et al., 1986; Anderson et al., 1986, 1987; and Cromeans et al., 1987), two of which are derived from separate lines of persistently-grown HM-175. It has been suggested that, in the case of one of the HM-175 cytopathic variants (Anderson et al., 1987), that the cytopathic nature and mechanism of persistence is associated with an alteration in the capsid polypeptide composition. Although this possibility cannot be ruled out, nucleotide sequence analysis of the long-term persistently grown HAS-15, which causes cell degeneration when used for an acute infection at high multiplicity of infection revealed that within the first 700 nucleotides of the VP1 molecule or the most surface exposed and potentially variable capsid polypeptide within other picornaviruses, there was only a single nucleotide difference when compared to the nucleotide sequence of lower passage (20 times) HAS-15 (Ovchinnikov et al., 1985).

The industry is lacking a process for reliably and economically reproducing milligram quantities of hepatitis A virus from cell culture propagation.

SUMMARY OF THE INVENTION

The invention is a process for cell culture propagation of hepatitis A virus. The process involves purifying hepatitis A virus particles produced in cell cuture.

These hepatitis A virus particles are used for infecting cells being cultivated in a cell culture media. The hepatitis A particles suitable for use in this invention must have a cytopathic effect in the infected host cells that are selected for culturing the hepatitis A virus. After developing the cytopathic effect in the infected cells, the hepatitis A viruses cause the infected cells to degenerate and lyse and the virus is released into the media. Isolation of the released hepatitis A virus then occurs.

The preferred cells for use in this invention are FRhK4 (foetal rhesus monkey kidney) cells. The preferred virus particles for use in this invention are hepatitis A, strain HAS-15 particles and which have an antigen coded by a nucleotide sequence according to FIG. 1.

BRIEF DESCRIPTION OF THE DRAWINGS

FIG. 1 illustrates a comparison of HAS-15 VP1 nucleotide sequence.

FIGS. 6A-6C illustrate a degenerative effect of a high multiplicity HAS-15 infection in FRhK4 cells at 2 to 3 weeks post-infection.

DETAILED DESCRIPTION OF THE INVENTION

Approaches to cell culture propagation of hepatitis A virus (HAV) have utilized either acute passage of infected cell lysates/supernatants into uninfected cells or the passage of persistently-infected cells. The data presented demonstrates that the growth and recovery of purified virus from FRhK4 cells persistently infected with HAS-15 HAV decreased over a 2 to 3 month period. In contrast, high multiplicity acute infection of FRhK4 cells with purified HAS-15 HAV resulted in degeneration of the cell monolayer 2 to 3 weeks later. Large scale propagation of acutely infected cells followed by traditional picornavirus purification procedures reproducibly yielded milligram amounts of purified virus. Comparison of the nucleic acid and derived amino acid sequence of VP1 derived from the HAS-15 HAV which caused cell degeneration revealed a single nucleotide difference which results in a homologous amino acid change when compared to published sequences of cloned HAS-15.

The data presented demonstrates that growth of cell culture adapted HAV in an acute, high multiplicity infection reproducibly yields milligram amounts of purified virus. The continued high yield from the use of the acute infection method and the reproducible recovery of purified virus has been facilitated by the fact that HAS-15 is highly adapted to FRhK4 cells (passaged approximately 60 times in persistently infected cells) and that these cells respond to growth stimuli such as the addition of fresh media by increasing the number of cells available for HAV replication and growth.

The process of this invention can be performed by using the materials and methods of the following Example. The following materials and methods represent the elements and procedures of the preferred embodiment of the invention. The Example is better understood by reference to the Figures and their following explanation. FIG. 1 is a comparison of HAS-15 VP1 nucleotide sequence (A) as published by Ovchinnickov et al., 1985, determined from cloned cDNA and (B) generated from viral RNA purified from long term persistently infected cells using primer-directed dideoxynucleotide chain termination. Underlined areas indicate the position of synthetic oligonucleotide primers within the sequence determined, with the fourth primer being located 40 nucleotides further toward the 3' end.

Figure 2:
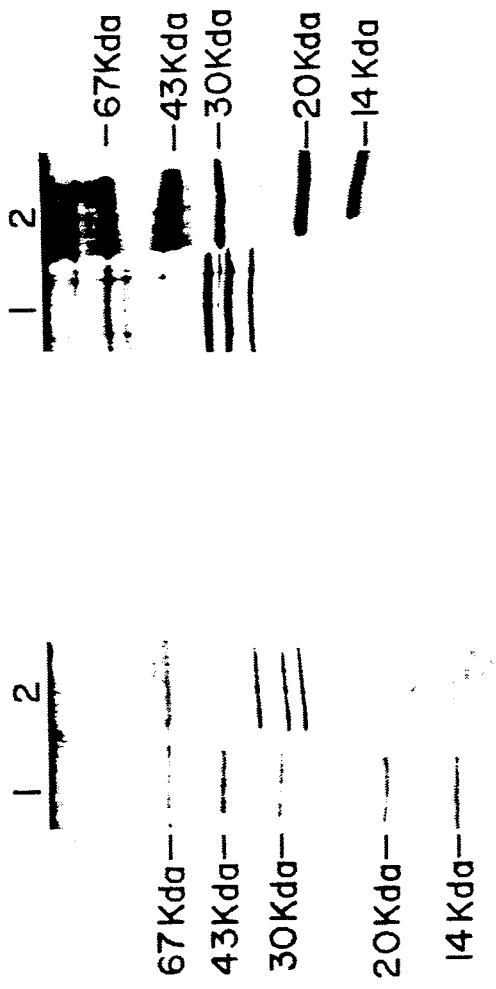
FIGS. 2A and 2B illustrate silver stained SDS-PAGE separated HAV polypeptides.

FIGS. 2A and 2B are silver stained SDS - PAGE separated HAV polypeptides. Panel 2A - 1 is sucrose gradient purified 160S HAV from long-term persistently infected FRhK4 cells. 2. Molecular weight markers are: 67Kda (bovine serum albumin), 43Kda (ovalbumin), 30Kda (carbonic anhydrase), 20 Kda (trypsin inhibitor), and 14.4 Kda (lactalbumin). Panel B - 1 is sucrose gradient purified 160S HAV from acutely infected FRhK4 cells. 2. Molecular weight markers are as described above.

Figure 3:
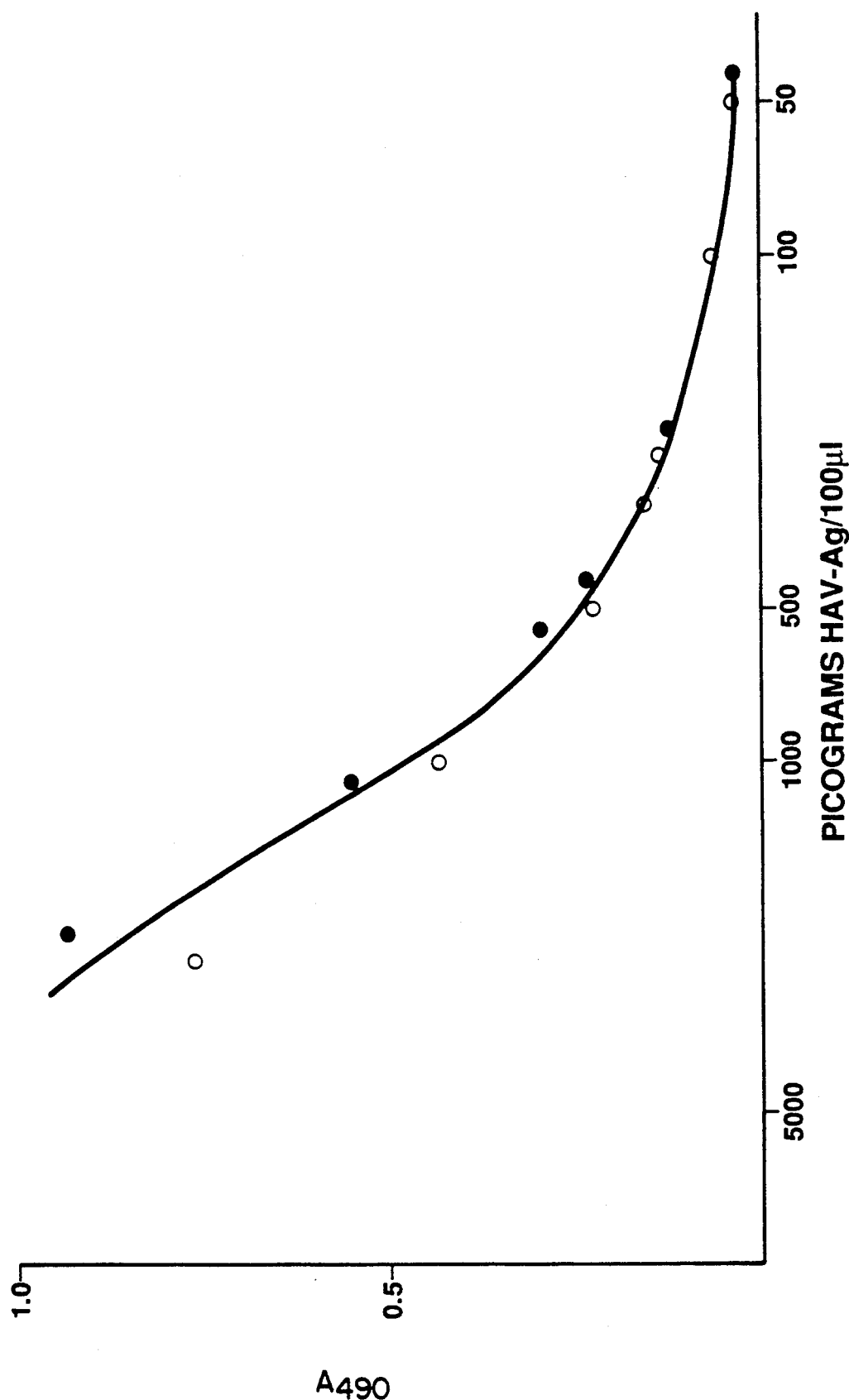
FIG. 3 illustrates an enzyme immunoassay titration.

FIG. 3 is an enzyme immunoassay titration. Dilutions of two separate preparations of purified 160S HAV, which had been quantitated by the $OD_{260}$ method, were evaluated by HAV-AG EIA (Wheeler et al., 1986b) to determine the minimal amount of HAV-AG reliably detectable. ●=preparation 1285-37CF; ○=preparation 685-16CF.

Figure 4:
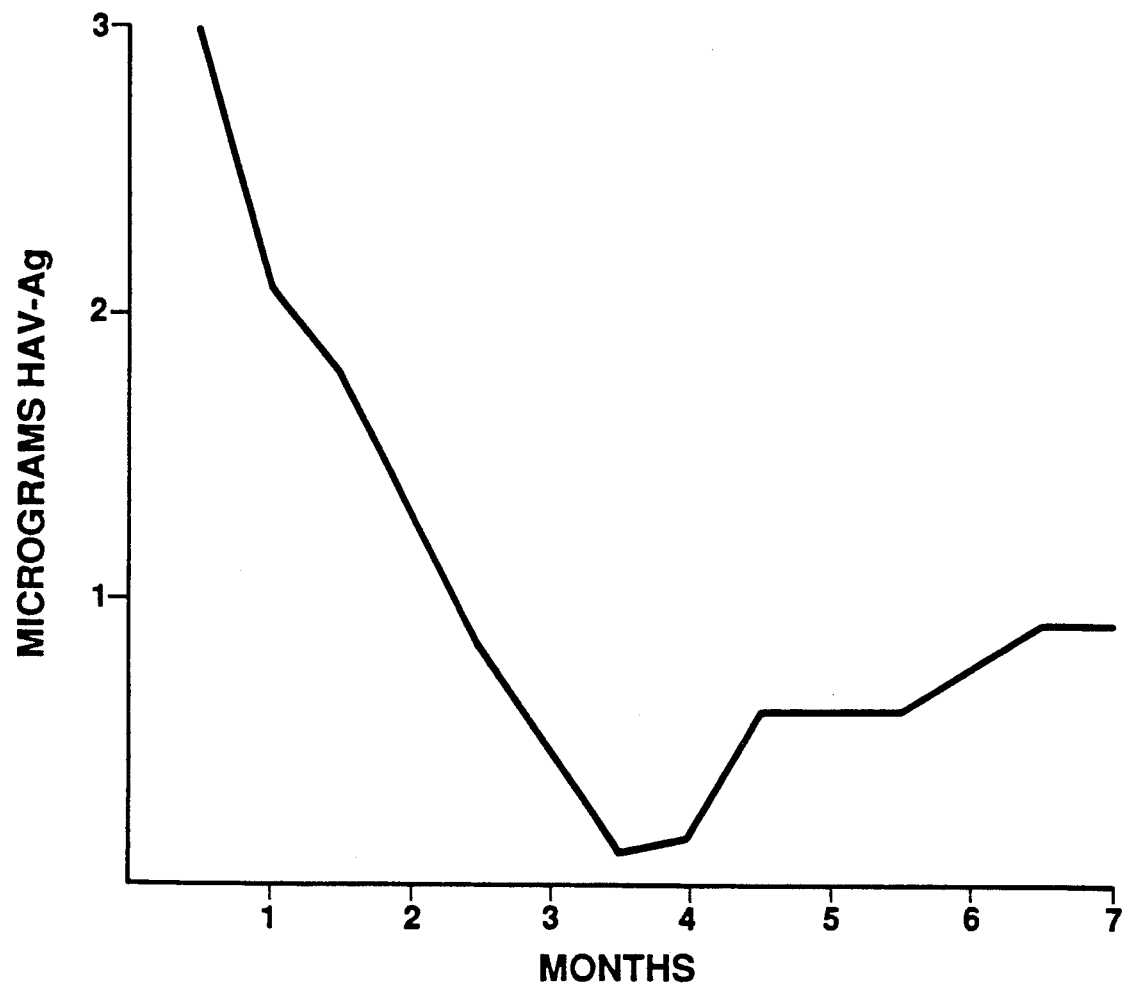
FIG. 4 illustrates a long-term production of HAS-15 HAV in persistently infected FRhK4 cells.

FIG. 4 is a graph of long-term production of HAS-15 HAV in persistently infected FRhK4 cells. Representative samples from FRhK4 cells which were inoculated with cell-culture adapted HAS-15 and carried as persistently-infected cells as described in the results. HAV-Ag present in the media and cells was quantitated by HAV-AG-EIA end point titration. Values are the total amount of HAV-Ag (supernatant and cell lysate) at each of the designated time points.

Figure 5A:
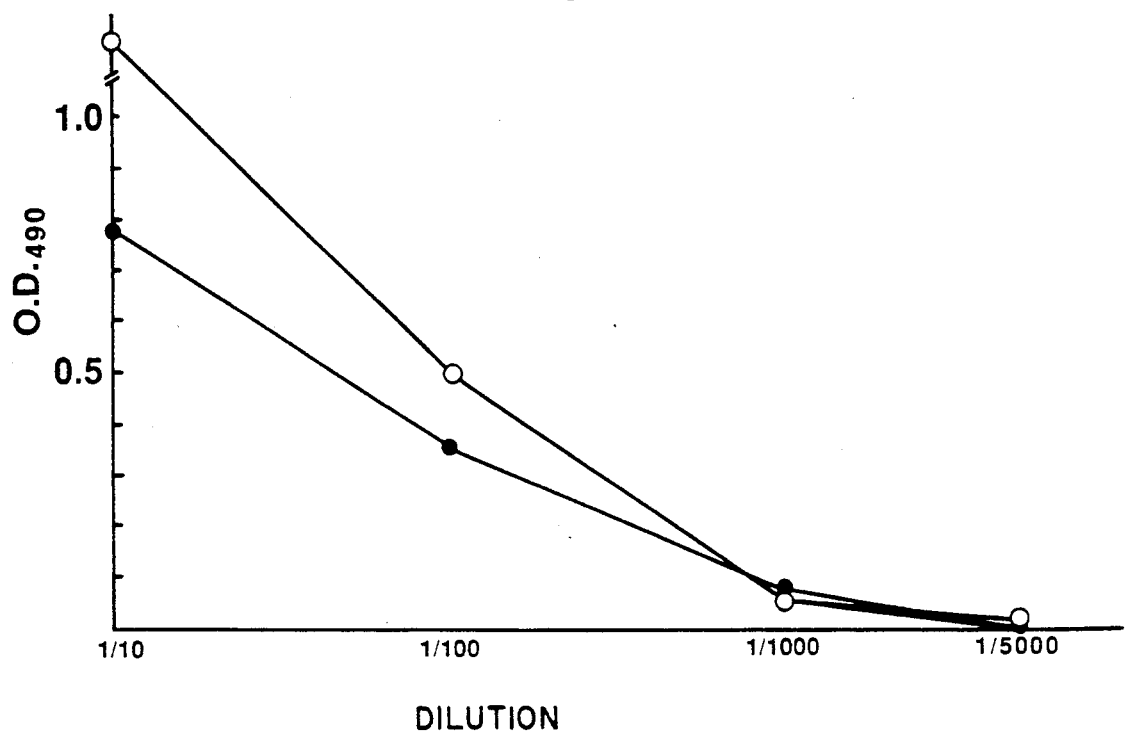
FIGS. 5A and 5B illustrate an enzyme immunoassay end point titration comparison of HAV-Ag.
Figure 5B:
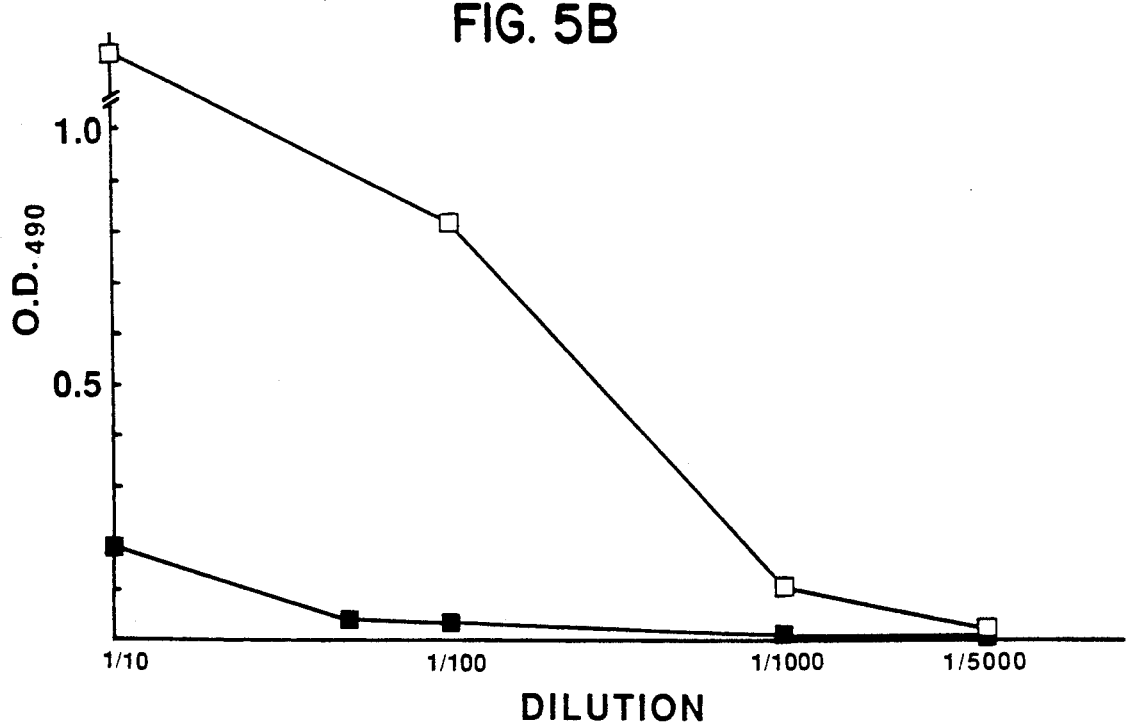

FIGS. 5A and 5B are an enzyme immunoassay end point titration comparison of HAV-Ag in (5A) acutely infected cells (○) and media (●) and (5B) long-term persistently infected cells (□) and media (■).

FIGS. 6A-6C are a photomicrograph of the degenerative effect of high multiplicity HAS-15 infection in FRhK4 cells at 2 to 3 weeks post-infection. FIG. 6A represents FRhK4 cells pass 86; (B) high multiplicity HAV-infected (approximately 300 infectious particles per cell) FRhK4 cells pass 86; and (C) long-term (>2 years) persistently-infected FRhK4 cells.

EXAMPLE

Large Scale Growth of Persistently Infected Cells. FRhK4 cells, persistently infected with HAS-15, carried by splitting 1:3 every 4 weeks over a three year period, were expanded for large scale virus production. Cell factories with 6000 cm² of surface area (Nunc Inc., Denmark) were seeded with these persistently infected cells from 10 confluent T-150 cm² tissue culture flasks (Corning Glassworks, Corning, N.Y.). Cells were released by treatment with 0.05 percent trypsin—0.02 percent EDTA for 15 minutes at 37° C. The trypsinized cell suspension was transferred into 1000 ml of Williams Medium E supplemented with 2 mM L-glutamine, 0.1 mm MEM nonessential amino acids, 0.2 percent sodium bicarbonate, 10 mM HEPES, 50 ug/ml gentamicin, 2 ug/ml of amphotericin B, and 10 percent heat-inactivated fetal calf serum. All media components for cell culture were from Gibco Laboratories, Life Technologies, Grand Island, N.Y. and Chagrin Fall, Ohio, with the exception of fetal calf serum which was from Hy-Clone Laboratories, Logan, Utah. The supplemented medium containing the cells was transferred into a single cell factory and incubated at 37° C. The medium was changed after 2 weeks and cells and medium were then harvested at four weeks. Cells were harvested by trypsinization at room temperature, fresh media supplemented as described above was added to residual cells in the cell factories and the cycle of growth, harvesting, and reseeding repeated.

Large Scale Growth of Acutely Infected Cells. FRhK4 cells (passages 78-84) were grown to confluency (using the media described above) in 850 cm² roller bottles (Corning, Corning, N.Y.). Cells were inoculated with the 160S sucrose density fraction of HAS-15 purified from long-term persistently infected FRhK4 cells. The multiplicity of infection was 300 infectious particles per cell as determined by radioimmunofocus assay. The inoculum was diluted in media containing 2 percent fetal calf serum. After rotation at 37° C. for two hours, complete media was added with continued incubation at 37° C. Three days later, acutely infected cells from two 850 cm² roller bottles were trypsinized and transferred to 6000 cm² Nunc cell factories as described above. The progression of HAV infection was evaluated by microscopic evaluation of a 600 cm² single layer Nunc tray containing acutely infected cells. Media was harvested every two weeks, and additional uninfected FRhK4 cells from two 850 cm² roller bottles added when cell degeneration was greater than 75 percent.

Virus Purification. Virus from large volumes of media was concentrated using one of two procedures. (1) Polyethylene glycol (PEG) and NaCl were added to a final concentration of 6.7 percent and 2.3 percent, respectively, and after 12 to 16 hours at 4° C., the precipitate was pelleted using a CF32ti continuous flow rotor (Beckman Instruments, Inc. Fullerton, Calif.) as previously described (Wheeler et al., 1986). The pellet was resuspended in 50 mM Tris pH 7.5-100 mM NaCl and NP-40 added to a final concentration of 1 percent. (2) Alternatively, the media was concentrated 10 to 20 fold by ultrafiltration using a 100,000 MW cut off hollow fiber filter (Amicon DC10LXR Amicon Corp., Danvers, Mass.) and then precipitated with 6.7 percent polyethylene glycol and 2.3 percent NaCl. The PEG precipitate was pelleted at 12,000×g for 30 minutes, resuspended in 50 mM Tris pH 7.5-100 mM NaCl, and NP-40 added at a final concentration of 1 percent.

As 80-90 percent of the virus produced in the persistently infected cells was cell-associated, cells harvested once every four weeks were frozen and thawed three times, followed by the addition of NP-40 to a final concentration of 1 percent and insoluble debris pelleted at 12,1000×G for 10 minutes at 4° C.

The 1 percent NP-40 soluble fraction from cells or media was treated with DNase I (10 ug/ml final concentration, Sigma, St. Louis, Mo.) in the presence of 20 mM $MgCl_2$ for 30 minutes at room temperature. The solution was then digested with trypsin (1 mg/ml final concentration,, Sigma) at 37° C. for 1 hour. After cooling to room temperature, SDS or SLS was added to a final concentration of 1 percent, and the virus pelleted by centrifugation at 30,000 RPM in a Type 35 rotor (Beckman) for 3.5 hours at 11° C. The pellet was resuspended in 50 mM Tris, pH 7.5, containing 100 mM NaCl and 0.002 percent phenol red. Viral aggregates were disrupted by the addition of 200 ul of 1 M dibasic sodium phosphate for each ml of viral solution, followed by neutralization with 100 ul of 1M acetic acid for each 200 ul of dibasic phosphate added. Sodium lauryl sarcosyl was added at a final concentration of 1 percent and the solution was centrifuged at 25,000 RPM in an SW 27 rotor (Beckman) at 15° C. for 8 hours through a 30 percent w/v sucrose cushion prepared in 25 mM Tris acetate, pH 7.5, containing 1M NaCl and 1 percent bovine serum albumin. The material which pelleted through the 30 percent sucrose cushion was resuspended in 50 mM Tris, pH 7.5, containing 100 mM NaCl (TNbuffer) and 1 percent sodium laryl sarcosyl and overlayed onto a preformed linear CsCl gradient (1.079 $gm/cc^3$-1.582 $gm/cc^3$) and centrifuged at 25,000 RPM in an SW 27 rotor at 4° C. for 24 hours. Fractions (1.0 ml) were collected from the top and those fractions positive by enzyme immunoassay for HAV antigen (Wheeler et al., 1986a) and having a buoyant density of 1.30 $gm/cc^3$-1.35 $gm/cc^3$ were pooled, concentrated and dialyzed into TN buffer using a Centriflo cone having a 25,000 MW cut off (Amicon Corp.). The concentrated pool was layered onto a 7.5-45 percent sucrose gradient in TN buffer and centrifuged in an SW41 rotor at 36,000 RPM for 90 minutes at 4° C. Fractions (0.5 ml) were collected from the top of the gradient and those positive for HAV antigen in the 160S region of the gradient were pooled, concentrated, and dialzyed against TN buffer using a Centriflo cone as described above.

The quantity of purified virus was determined by assuming that the optical density of a 1 mg/ml concentration of virus measured at 260 nm was equivalent to 7.7 (Rueckert 1971, 1976; Rueckert and Pallansch, 1981).

Radioimmunofocus Assay. FRhK4 cells (pass 72-90) were grown in 60 mm Lux plates (Miles Laboratories, Naperville, Ill.) to confluency in the media described above and then inoculated with 10 fold dilutions of purified virus. The plates were processed as described by Lemon et al., (1983) using iodinated HAV antibody (HAVAB Kits, Abbott Laboratories, North Chicago, Ill.) to evaluate the quantity of infectious virus.

Enzyme Immunoassay for HAV Antigen (HAV-AG EIA). Detection of HAV antigen was done using the IgG fraction of rabbit anti-HAV as the capture antibody and the biotinylated IgG fraction of chimpanzee hyperimmune anti-HAV as the detector antibody as previously described (Wheeler et al., 1986b). Color development was with Detek-1-HRP (Enzo Biochem., NY, N.Y.) and phenylenediamine (Sigma, St. Louis, Mo.).

Polyacrylamide Gel Electrophoresis. Evaluation of virus purity was achieved by electrophoresis on 12 to 27 percent gradient acrylamide gels as described by Wheeler et al. (1986b).

RNA Extraction and Nucleotide Sequencing. RNA was extracted from purified virus by digestion with addition of an equal volume of 2 mg/ml proteinase K (BRL, Gaithersburg, Md.) in 20 mM Tris, pH 7.5, containing 10 mM EDTA and 1 percent SDS at 45° C. for 1 hour. The digested sample was then phenol:-chloroform extracted and ethanol precipitated. Quantitation of RNA was determined spectrophotometrically assuming that an optical density at 260 nm (O.D. 260) of 1.0 is equivalent to 40 ug/ml. Sequencing of the viral RNA (0.7-2ug per set of reactions) was performed by incorporative dideoxynucleotide termination as described by Sanger et al., (1977). Synthetic oligonucleotides complementary to selected regions of the HAV VP1 published sequence were hybridized to viral RNA and extended with reverse transcriptase (Life Sciences, St. Petersburg, Fla.) in the presence of $^{35}S$ dATP and dideoxynucleotide triphosphates.

The results of the Example are as follows.

Virus Quantitation. In cell culture, quantitation of HAV has been by antibody dependent detection methods because the virus grows slowly and is not cytopathic. In addition, quantitation of HAV from sources such as stool, liver, or serum is complicated by many variables including the presence of naturally occurring antibody (Bradley et al., 1982), aggregation of viral particles, and interference by normal serum or cellular components (Seelig et al., 1984). The availability of large amounts of purified HAV from persistently infected cells allowed the comparison of traditional approaches for protein quantitation with antibody dependent approaches used for HAV detection.

The purity of HAV (HAS-15) preparations derived from long-term, persistently infected FRhK4 cells was assessed by gel electrophoresis. As shown in FIG. 2A, Lane 2, greater than 98 percent of the silver stained protein is accounted for by the three larger viral polypeptides: VP1, VP3, and VP2. Purified HAV (dilutions of two preparations) was used to evaluate the reproducibility and sensitivity of the HAV-Ag EIA when compared to virus quantitation by the $OD_{260}$ method. The data, shown in FIG. 3, indicates that the antibody dependent assay, using purified HAV, is sensitive and reproducible. This HAV-Ag EIA was subsequently used to determine the recovery of virus during purification from cell culture, assuming that 200 picograms of HAV antigen was the lower limit of reliable detection (0.1 $OD_{490}$). Evaluation of the number of infectious particles present as determined by the radioimmunofocus assay (RIFA), which measures the synthesis of HAV antigen (HAV-Ag), revealed that approximately one-third of the physical particles were infectious and that the radioimmunofocus assay was 4 to 5 orders of magnitude more sensitive than the HAV-AG EIA for detection of virus.

Parameters Affecting Virus Yield in Persistently Infected Cells. Published recoveries of purified virus from persistently infected cells were calculated to be equivalent to 30 ug per cell factory (Wheeler et al., 1986b). However, subsequent purifications repeatedly yielded 10 fold less virus than expected, of which a representative recovery is shown in column 1, Table 2. Therefore, the standardized enzyme immunoassay was used to evaluate various parameters to ascertain the discrepancy between the reported recovery and those subsequently obtained.

The effect of the concentration of fetal calf serum (FCS) and the duration of time in culture on the production of virus is shown in Table 1. The production of HAV appears to be somewhat enhanced by a reduction in FCS to 10 percent, but the most striking effect on virus production was due to the increase of cell culture time. When the cells were cultured for longer than 2 weeks, the need to refeed cells with fresh media in order to prevent degeneration and death was an important co-variable which apparently contributed to increased virus production as shown in lines 7 and 8 of Table 1.

Under these cell culture conditions, over 99 percent of the virus produced was cell associated while 1 percent was released into the cell culture supernatant (Table 1). Several experiments were performed where persistently infected cells were superinfected with HAS-15. The approach did not result in an increase in virus irrespective of time of culture or concentration of FCS (data not shown). The scale-up of virus production in persistently infected FRhK4 cells from 150cm$^2$ flasks (data in Table 1) to 6,000 cm$^2$ factories using 10 percent FCS and a 4 week growth period with refeeding with fresh media after 2 weeks resulted in a 4 to 7 fold increase in HAV recovery when compared to the previously published method for large scale production of virus (Table 2, compare column 1 to columns 2 to 4).

Time Course of Persistent HAV Infection. An evaluation of HAV antigen produced over a 7-month time period by persistently infected cells was performed by inoculating a single T150 flask containing high passage FRhK4 cells (pass 258 at inoculation) with a cell lysate from HAS-15 HAV (pass 23 at inoculation). Two weeks later, the media was harvested and the cells split 1:3. After an additional two weeks growth, the media from the three flasks was harvested, the cells in one flask split 1:3 while the cells from the remaining two flasks were harvested by scraping, and frozen and thawed three times, sonicated for one minute and the cell debris pelleted by centrifugation at 2000×g for 10 minutes. The HAV-Ag present in the harvested cells and supernatant was then evaluated. The results (FIG. 4) indicated that the amount of virus produced during initial infection was substantially higher than during the later period of the persistent infection. Longer term passage of the persistently infected cells resulted in a leveling off of virus production but at much lower levels than in the first three months of infection.

Comparison of Virus Production in Acutely and Persistently Infected Cells. The amount of viral antigen produced in acutely infected FRhK4 cells was compared to that generated in persistently infected cells. Since the data in FIG. 4 suggested that initial infection of cells with HAV resulted in higher levels of virus production, acute infection was performed by inoculating uninfected FRhK4 cells with 300 radioimmunofocus units of purified persistently grown HAS-15 per cell. The amount of virus produced by these two virus-cell systems as assessed by the HAV-Ag EIA are shown in FIGS. 5A and 5B. The results indicated that more virus was produced by the acutely infected cells. The majority of the virus was present in the media while most of the virus within the long-term persistently-infected cells was cell-associated.

In addition to the increased amount of virus produced during the acute infection of FRhK4 cells with virus derived from persistently infected cells, acute infection resulted in degeneration of the cell monolayer approximately two weeks after infection (FIG. 6, Panel B), when compared to uninfected cells (FIG. 6, Panel A). For comparative purposes, the long term high passage persistently infected FRhK4 cells grown under the same conditions are shown in FIG. 6, Panel C. Attempts at superinfection of the high passage FRhK4 cells persistently infected with HAS-15 has consistently failed to induce cell degeneration. In addition, inoculation of BSC-1 cells (passage 80) with 300 infectious particles per cell failed to induce any cell degeneration over a one month period, suggesting that this degeneration effect is virus-cell specific.

Virus Yield from Large Scale Propagation of Acutely Infected Cells. The quantity of HAV produced from FRhK4 cells acutely infected with HAS-15 was 5 to 10 fold greater than the amount of virus obtained from the same number of persistently infected cells (Table 2). In practice, there was little need to lyse cells because of the high degree of cell destruction that occurred over the 4 week culture period and supernatant media alone was used for virus purification. The purity of the recovered virus was assessed by silver staining of PAGE separated polypeptides and revealed the presence of the three viral capsid proteins (FIG. 2B, Lane 1) and no other protein bands that reacted with rabbit anti-160S sera after Western blotting (data not shown).

Nucleotide Sequence Analysis of Long-Term Persistently Grown HAS-15 HAV. A partial nucleotide sequence of HAS-15 HAV from cloned cDNA indicated that the VP1 molecule contained an eighteen nucleotide deletion near the amino terminus (Ovchinnikov et al., 1985). This deletion is unique to this strain when compared to other HAV isolates sequenced thus far (Najarian et al., 1985; Linemeyer et al., 1985; and Baroudy et al., 1985). The virus used by Ovchinnikov et al., (1985) for sequencing was obtained after approximately 20 cell culture passages. The virus obtained from persistently infected cells and used for the acute infection of FRhK4 cells has been passaged approximately 60 times. This same virus also produces cell degeneration in culture. The sequence of the first 700 nucleotides of the VP1 molecule of the passage 60 HAS-15 using primer-directed sequencing of the viral RNA was compared to the sequences obtained by Ovchinnikov et al., (1985) using cloned cDNA (passage 20 HAS-15) and is shown in FIG. 1. The data reveal that the nucleotide sequence is highly conserved, with a single A to G nucleotide substitution in the same region as the eighteen nucleotide deletion. This substitution results in a homologous amino acid change from isoleucine to methionine. The eighteen nucleotide deletion within HAS-15 generates a VP1 molecule which migrates distinguishably faster on polyacrylamide gels compared to other characterized isolates of HAV, i.e., HM-175 and MS-1 (unpublished observation, Robertson, et al., 1987).

TABLE 1

EFFECT OF FETAL CALF CONCENTRATION and GROWTH TIME ON HAV-Ag PRODUCTION IN LONG-TERM PERSISTENTLY-INFECTED FRhK4 CELLS

| FETAL CALF SERUM (%) | TIME (Wks.) | TOTAL HAV-Ag (ng)* | |
|---|---|---|---|
| | | CELL LYSATE | SUPERNATANT |
| 20 | 2 | 600 | <0.2 |
| 20 | 2 | 726 | <0.2 |
| 20 | 2 | 504 | <0.2 |
| 10 | 2 | 636 | <0.2 |

TABLE 1-continued

EFFECT OF FETAL CALF CONCENTRATION and GROWTH TIME ON HAV-Ag PRODUCTION IN LONG-TERM PERSISTENTLY-INFECTED FRhK4 CELLS

| FETAL CALF SERUM (%) | TIME (Wks.) | TOTAL HAV-Ag (ng)* | |
|---|---|---|---|
| | | CELL LYSATE | SUPERNATANT |
| 20 | 3** | 76 | 91 |
| 10 | 3** | 94 | 156 |
| 20 | 4** | 912 | <0.2 |
| 10 | 4** | 1500 | <0.2 |

*Total HAV-Ag present in T-150 cells and media as determined by HAV-Ag EIA
**Media in flasks was changed to prevent cell death.

TABLE 2

COMPARISON OF HAV YIELD FROM PERSISTENTLY-INFECTED AND ACUTELY INFECTED FRhK4 CELLS

| | PERSISTENTLY INFECTED CELLS | | | | ACUTELY INFECTED CELLS | | | |
|---|---|---|---|---|---|---|---|---|
| Preparation (date) | 1285 | 586 | 686 | 1086 | 187 | 387 | 587 | 687 |
| Conditions | | | | | | | | |
| Fetal Calf Serum (%) | 20 | 10 | 10 | 10 | 10 | 10 | 10 | 10 |
| Duration of Culture (wk) | 2 | 4 | 4 | 4 | 4 | 4 | 4 | 4 |
| Cell Factories Processed (#) | 37 | 16 | 16 | 48 | 62 | 46 | 38 | 67 |
| Purification Step | | | | | | | | |
| Sucrose Cushion Pellet* (mg) | 0.104 | 0.400 | 0.480 | — | — | 2.7 | — | — |
| CsCl Peak** (mg) | 0.090 | 0.155 | 0.108 | 0.740 | 2.2 | 2.2 | 2.1 | 5.8 |
| Virus/Cell Factory (ug) | 2.4 | 9.7 | 6.8 | 15.4 | 35 | 48 | 56 | 72 |

*HAV-Ag EIA end point titration
**OD$_{260}$ Quantitation

What is claimed is:

1. A process for cell culture propagation of hepatitis A virus comprising the steps of:
    a) acutely infecting susceptible cells with strain HAS-15 hepatitis A viral particles at a multiplicity of infection of approximately 300 infectious viral particles per cell, said infection resulting in cell lysis and subsequent release of viral particles; and
    b) isolating and purifying said released viral particles of step a).

2. The process of claim 1 wherein acute injection is maintained by addition of uninfected cells when 75% of the original cells have lysed.

3. The process of claim 1 wherein said susceptible cells of step a) are FRhK4 foetal rhesus monkey kidney cells.

4. The process of claims 1 or 3 wherein said hepatitis A particles have an antigen coded by a VP1 region nucleotide sequence according to FIG. 1.

* * * * *